(12) United States Patent
Lee et al.

(10) Patent No.: US 9,442,099 B2
(45) Date of Patent: Sep. 13, 2016

(54) HYDROGEN SENSOR AND METHOD OF MANUFACTURING THE SAME

(71) Applicant: Industry-Academic Cooperation Foundation, Yonsei University, Seoul (KR)

(72) Inventors: Woo Young Lee, Seoul (KR); Heon Lee, Seoul (KR); Byueng Jin Chang, Seoul (KR); Seung Hyun Lee, Incheon (KR); Jun Min Lee, Seongnam si (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 439 days.

(21) Appl. No.: 13/832,865

(22) Filed: Mar. 15, 2013

(65) Prior Publication Data
US 2013/0255358 A1 Oct. 3, 2013

(30) Foreign Application Priority Data

Mar. 19, 2012 (KR) ........................ 10-2012-0027626

(51) Int. Cl.
| | |
|---|---|
| *G01N 7/00* | (2006.01) |
| *G01N 9/00* | (2006.01) |
| *B23P 17/04* | (2006.01) |
| *G01R 31/28* | (2006.01) |
| *G01N 33/00* | (2006.01) |
| *C23C 30/00* | (2006.01) |
| *G01N 27/12* | (2006.01) |
| *C23C 14/20* | (2006.01) |

(52) U.S. Cl.
CPC ......... *G01N 33/0036* (2013.01); *C23C 14/205* (2013.01); *C23C 30/00* (2013.01); *G01N 27/128* (2013.01); *G01N 33/005* (2013.01)

(58) Field of Classification Search
None
See application file for complete search history.

(56) References Cited

U.S. PATENT DOCUMENTS

| | | | | |
|---|---|---|---|---|
| 6,855,025 | B2* | 2/2005 | Iwasaki et al. | 445/24 |
| 7,056,446 | B2* | 6/2006 | Nagase et al. | 216/57 |
| 7,104,111 | B2* | 9/2006 | Monty et al. | 73/23.2 |

(Continued)

FOREIGN PATENT DOCUMENTS

KR 10-2011-0075841 7/2011

OTHER PUBLICATIONS

Ing-Shin Chen et al.,"Micro-Machined Thin Film H2Gas Sensors" DOE Hydrogen and Fuel Cells 2003 Annual Merit Review, (2003).

(Continued)

*Primary Examiner* — Lisa Caputo
*Assistant Examiner* — Jermaine Jenkins
(74) *Attorney, Agent, or Firm* — Lex IP Meister, PLLC (57) ABSTRACT

A method of the invention includes preparing a mold having a hydrogen detection part pattern, a nanogap pattern and a base to be formed on a hydrogen sensor substrate; preparing a material to which the patterns are transferrable; forming the hydrogen sensor substrate by bringing the mold into contact with the material to thus transfer the patterns to the material and then detaching the mold from the material to which the patterns are transferred, the hydrogen sensor substrate having a base part corresponding to the base, a plurality of hydrogen detection parts erected from the base part and corresponding to the nanogap pattern and a plurality of nanogaps formed between the hydrogen detection parts and corresponding to the hydrogen detection part pattern; and forming, on the hydrogen sensor substrate, a thin film of a transition metal or an alloy thereof to be expanded by hydrogen.

12 Claims, 11 Drawing Sheets

(56) References Cited

U.S. PATENT DOCUMENTS

| | | | |
|---|---|---|---|
| 7,319,069 B2* | 1/2008 | Den et al. | 438/667 |
| 7,335,408 B2* | 2/2008 | Kyotani et al. | 428/34.1 |
| 7,445,742 B2* | 11/2008 | Chen et al. | 264/293 |
| 7,762,121 B2* | 7/2010 | Ng et al. | 73/23.31 |
| 7,875,194 B2* | 1/2011 | Lee et al. | 216/2 |
| 8,023,109 B2* | 9/2011 | Yamamichi et al. | 356/72 |
| 8,087,151 B2* | 1/2012 | Park et al. | 29/592.1 |
| 8,187,865 B2* | 5/2012 | Yun et al. | 435/287.2 |
| 8,468,872 B2* | 6/2013 | Lee et al. | 73/23.2 |
| 8,852,979 B2* | 10/2014 | Min et al. | 438/46 |

OTHER PUBLICATIONS

Frédéric Favier, et al. "Hydrogen Sensors and Switches from Electrodeposited Palladium Mesowire Arrays," Science 293, 2227-2231 (Sep. 21, 2001).

* cited by examiner

HYDROGEN SENSOR AND METHOD OF MANUFACTURING THE SAME

CROSS REFERENCE TO RELATED APPLICATION

The present application claims priority from Korean Patent Application Number 10-2012-0027626 filed on Mar. 19, 2012, the entire contents of which application are incorporated herein for all purposes by this reference.

BACKGROUND OF THE INVENTION

1. Field of the Invention

The present invention relates to a method of manufacturing a hydrogen sensor, and more particularly, to a hydrogen sensor and a method of manufacturing the same, in which a thin film made of a transition metal or an alloy thereof is used.

2. Description of Related Art

Active studies on hydrogen energy are underway since the hydrogen energy has merits in that it is renewable and does not create environmental pollution.

However, since there is a danger in that hydrogen gas is vulnerable to explosion when it leaks into the surrounding atmosphere at a concentration of 4% or more, application in actual life is difficult unless the safety of use is guaranteed. Therefore, studies on the utilization of hydrogen energy as well as the development of a hydrogen gas detection sensor (hereinafter, simply referred to as a 'hydrogen sensor'), which can detect the early stage of leakage of hydrogen gas when applied in practice, are underway.

Hydrogen sensors which have been developed up to the present include ceramic/semiconductor type sensors (catalytic combustion, thermoelectric or semiconductor thick film sensors), semiconductor device sensors (metal insulator semiconductor field effect transistor (MISFET) or metal oxide semiconductor (MOS) sensors), optical sensors, potentiometric/amperometric sensors, and the like.

The ceramic/semiconductor sensors typically use a change in electrical conductivity that occurs when gas contacts the surface of the ceramic semiconductor. Since the ceramic/semiconductor sensors are frequently heated in the air, metal oxides (e.g., ceramics, $SnO_2$, $ZnO$ or $Fe_2O_3$) that are stable at high temperatures are generally used. However, the ceramic/semiconductor sensors cannot detect high concentrations of hydrogen gas, since they are saturated in high concentrations of hydrogen gas, which is problematic.

The catalytic combustion sensors detect a change in combustion heat generated by an oxidation reaction which occurs due to the contact of combustible gas with the surface of the sensor. The advantages of these sensors are that output power is proportional to the concentration of gas, detection precision is high, and the sensor is less influenced by ambient temperature or moisture. However, this sensor requires a high operating temperature and has no selectivity, which is problematic.

In addition, the semiconductor device sensors (e.g. the MISFET or MOS sensor) and the optical sensors which use a gasochromic material, the optical transmittance of which varies depending on the absorption of hydrogen, use palladium (Pd) which has a great ability to absorb hydrogen. However, these sensors have a drawback in that, for example, the ability degrades when the sensors are repeatedly exposed to high concentrations of hydrogen gas.

Finally, the potentiometric/amperometric sensors are devices which electrochemically oxidize or reduce a gas that is to be detected and measure current flowing through an external circuit at that time. The potentiometric/amperometric sensors can be divided into an electrostatic sensor, a galvanic cell sensor, an ion electrode sensor, and the like depending on the principle of detection. Although these sensors have an ability to detect various types of gases, they suffer from the disadvantage whereby the methods of manufacturing the sensors are complicated and difficult.

Sensors that have been recently used in hydrogen detection technologies include a Pd thin-film sensor, a semiconductor sensor, such as an MISFET sensor, a carbon nanotube sensor, a titania nanotube sensor and the like (F. Dimeo et al., 2003 Annual Merit Review). However, despite the respective advantages of these technologies, the performance of these sensors is still dissatisfactory in terms of the initial concentration of hydrogen gas that can be detected, response time, detection temperature, drive voltage and the like, which can be regarded as key factors of a hydrogen sensor.

One technology that was recently developed discloses the use of the phenomenon whereby, when sites on which Pd particles can be generated are prepared using a graphite layer through the reaction between Pd and hydrogen, the resultant Pd particles are formed into a wire, in which Pd lattices are expanded and connected to each other as hydrogen is introduced into a functionalized substrate, thereby reducing electrical resistance (Penner et al. Science 293 (2001), 2227-2231). Here, the lattice expansion of Pd in response to the adsorption of hydrogen was experimentally observed, and an electrical signal was thereby detected by arraying the Pd nanoparticles in the form of a discontinuous wire. However, the disadvantages are that the method of manufacturing the sensor is complicated and the minimum concentration that can be detected is high.

In general, hydrogen detection sensors using a Pd thin film are widely used, since they exhibit hydrogen detection performance that is far better than those of sensors manufactured using other materials. In such hydrogen sensors in the related art, a method of expanding lattices by bringing the Pd particles into close contact with the substrate by applying a strong force to the Pd particles through sputtering, vapor deposition, or the like was used. However, the sensitivity to hydrogen was not high, since the amount of expansion was reduced by the force of bonding to the substrate. In addition, in the case in which the Pd particles are not bonded to the substrate, if the exposure to hydrogen is stopped after the Pd lattices are expanded upon exposure to hydrogen, the initial state was not restored due to the bonding force between the Pd particles, thereby entailing the disadvantage of low reproducibility. Furthermore, hydrogen sensors using Pd particles have other problems in that they react only to hydrogen having a high concentration and their initial resistance value changes when they are no longer exposed to hydrogen.

Although the hydrogen sensors of the related art have overcome some of the above-noted problems with existing hydrogen sensors, they fail as replacements for the existing hydrogen sensors for reasons pertaining to detection ability, sensitivity, stability, the speed of response at low concentrations, and the like.

Therefore, studies on materials and structures that can optimize hydrogen detection performance are underway, and attempts to improve hydrogen detection performance using nanomaterials are continually being made.

Pd, as a representative nanomaterial, has a property such that it reacts with hydrogen regardless of the surrounding environment, and exhibits a phenomenon in which its lattice constant increases when it chemically absorbs hydrogen gas, thereby showing increased resistance when current is induced.

Based on this phenomenon, recent studies on solid hydrogen sensors that react only to hydrogen using a Pd nanowire, the surface area of which is maximized, are actively underway. The hydrogen sensors using the Pd nanowire are adapted to detect hydrogen based on the phenomenon by which the resistance of the Pd nanowire changes depending whether or not hydrogen is present.

Methods of manufacturing the Pd nanowire that have been developed to date include a method using a highly oriented pyrolytic graphite (HOPG) template, a method using electron-beam lithography (EBL), a method using di-electrophoresis (DEP), and the like.

The method of using the HOPG template is a method of electrochemically producing a Pd nanowire on a nanotemplate of a substrate. However, this method has disadvantages in that the manufacturing process is complicated and time-consuming, and that the production yield is low, attributable to the resultant Pd nanowire, which is difficult to impart with a constant resistance value due to errors during the manufacturing process.

In addition, the method using EBL is a method of electrochemically forming a Pd nanowire after forming a nano-pattern on a substrate. However, this method has the disadvantages of low production yield and high manufacturing cost.

Likewise, the method using DEP is a method of producing a nanowire by forming a layer of a nanowire material on a substrate, followed by supplying a high-frequency alternating current (AC) power source through metal electrodes. However, this method has disadvantages in that the manufacturing process is complicated and the production yield is low, since it is impossible to produce a Pd nanowire having a uniform shape.

Therefore, the development of a novel manufacturing process, which can fabricate a Pd hydrogen sensor at a low cost and in a simple fashion while ensuring that the hydrogen detection performance of Pd is maintained unchanged, is required.

In addition, a method which forms nanogaps in a Pd thin film such that the nanogaps expand and contract depending on whether or not hydrogen is absorbed thereto and detects hydrogen based on the expansion and contraction of the nanogaps was proposed (Korean Patent No. 10-1067557). However, according to this method, the nanogaps are formed in a thin film formed on a substrate by applying stress to the thin film. Mass production is substantially impossible, since stress must be applied individually. In addition, the substrate of this technology is also limited to an elastic substrate.

The information disclosed in the Background of the Invention section is only for better understanding of the background of the invention, and should not be taken as an acknowledgment or any form of suggestion that this information forms a prior art that would already be known to a person skilled in the art.

BRIEF SUMMARY OF THE INVENTION

Various aspects of the present invention provide a novel method of manufacturing a hydrogen sensor which can simply fabricate a hydrogen sensor in a short time and at a low price, and replace a method of manufacturing a hydrogen sensor of the related art, which is complicated, takes a long time, and exhibits a poor yield, and a hydrogen sensor manufactured thereby.

Also provided are a low-price and high-performance hydrogen sensor which can accurately detect hydrogen by excluding an influence caused by an error in the manufacturing process and increasing the reproducibility of the reaction of the sensor to hydrogen, and a method of manufacturing the same.

Also provided are a method of manufacturing a hydrogen sensor which can mass-produce hydrogen sensors by forming nanogaps in a thin film using a simple scheme, and a hydrogen sensor manufactured thereby.

Also provided are a method of manufacturing a hydrogen sensor which can form nanogaps in a thin film depending on the purpose of a hydrogen sensor without being restricted by the type of a substrate, and a hydrogen sensor manufactured thereby.

In an aspect of the present invention, provided is a method of manufacturing a hydrogen sensor. The method includes the following steps of: preparing a mold which has a hydrogen detection part pattern, a nanogap pattern and a base which are to be formed on a hydrogen sensor substrate; preparing a material to which the patterns of the mold are transferrable; forming the hydrogen sensor substrate by bringing the mold into contact with the material to thus transfer the patterns of the mold to the material and then detaching the mold from the material to which the patterns are transferred, the hydrogen sensor substrate having a base part which corresponds to the base of the mold, a plurality of hydrogen detection parts which is erected from the base part and corresponds to the nanogap pattern, and a plurality of nanogaps which is formed between the hydrogen detection parts and corresponds to the hydrogen detection part pattern; and forming a thin film on the hydrogen sensor substrate, the thin film being made of a transition metal or an alloy thereof which is to be expanded by hydrogen.

According to an embodiment of the present invention, the hydrogen sensor substrate may be made of a flexible material or an inflexible material.

According to an embodiment of the present invention, the hydrogen sensor substrate may be made of an inflexible material, such as polyvinyl chloride (PVC), polyethylene terephthalate (PET) or polyethylene succinate (PES).

According to an embodiment of the present invention, the hydrogen sensor manufactured by the above-described method may be used as an on-current sensor.

According to an embodiment of the present invention, the hydrogen sensor substrate may be made of natural rubber, synthetic resin or polymer.

According to an embodiment of the present invention, the synthetic resin may be one selected from among butadiene-based rubber, isoprene-based rubber, chloroprene-based rubber, nitrile-based rubber, polyurethane-based rubber and silicone-based rubber. Preferably, the synthetic resin may be polydimethylsiloxane (PDMS).

According to an embodiment of the present invention, the transition metal may be one transition metal selected from among Pd, Pt, Ni, Ag, Ti, Fe, Zn, Co, Mn, Au, W, In and Al, and preferably, Pd.

According to an embodiment of the present invention, the alloy may be one selected from among Pd—Ni, Pt—Pd, Pd—Ag, Pd—Ti, Pd—Fe, Pd—Zn, Pd—Co, Pd—Mn, Pd—Au, Pd—W, Pt—Ni, Pt—Ag, Pt—Ag, Pt—Ti, Fe—Pt, Pt—Zn, Pt—Co, Pt—Mn, Pt—Au and Pt—W that can be expanded by hydrogen.

According to an embodiment of the present invention, a thickness of the transition metal may range from 8 nm to 12 nm.

According to an embodiment of the present invention, the method may further include the step of connecting electrodes in a direction perpendicular to a longitudinal direction of the nanogaps.

According to an embodiment of the present invention, a ratio of a height to a width of the nanogaps may be 1:x, where x<1.

In an aspect of the present invention, provided is a hydrogen sensor which includes: a hydrogen sensor substrate; a thin film formed on a surface of the hydrogen sensor substrate, the thin film being made of a transition metal or an alloy thereof that is to be expanded by hydrogen; and electrodes connected to the hydrogen sensor substrate. The hydrogen sensor substrate has a base part, a plurality of hydrogen detection parts erected from the base part, and a plurality of nanogaps formed between the hydrogen detection parts. The thin film is formed across the plurality of hydrogen detection parts and the plurality of nanogaps.

According to an embodiment of the present invention, the electrodes may be connected to the substrate in a direction perpendicular to a longitudinal direction of the nanogaps.

According to an embodiment of the present invention, a ratio of a height to a width of the nanogaps may be 1:x, where x<1.

According to embodiments of the present invention, hydrogen sensors having nanogaps can be mass-produced by a method different from a traditional method. In addition, hydrogen sensors having nanogaps can be mass-produced depending on purposes without being specifically restricted by the material of a substrate.

The methods and apparatuses of the present invention have other features and advantages which will be apparent from, or are set forth in greater detail in the accompanying drawings, which are incorporated herein, and in the following Detailed Description of the Invention, which together serve to explain certain principles of the present invention.

DETAILED DESCRIPTION OF THE INVENTION

Reference will now be made in detail to various embodiments of the present invention, examples of which are illustrated in the accompanying drawings. In the following, descriptions of technical parts that are well known in the art will be omitted. Although such descriptions are omitted, the characteristic features of the present invention will be apparent to a person having ordinary skill in the art from the following description taken in conjunction with the accompanying drawings.

Figure 1:
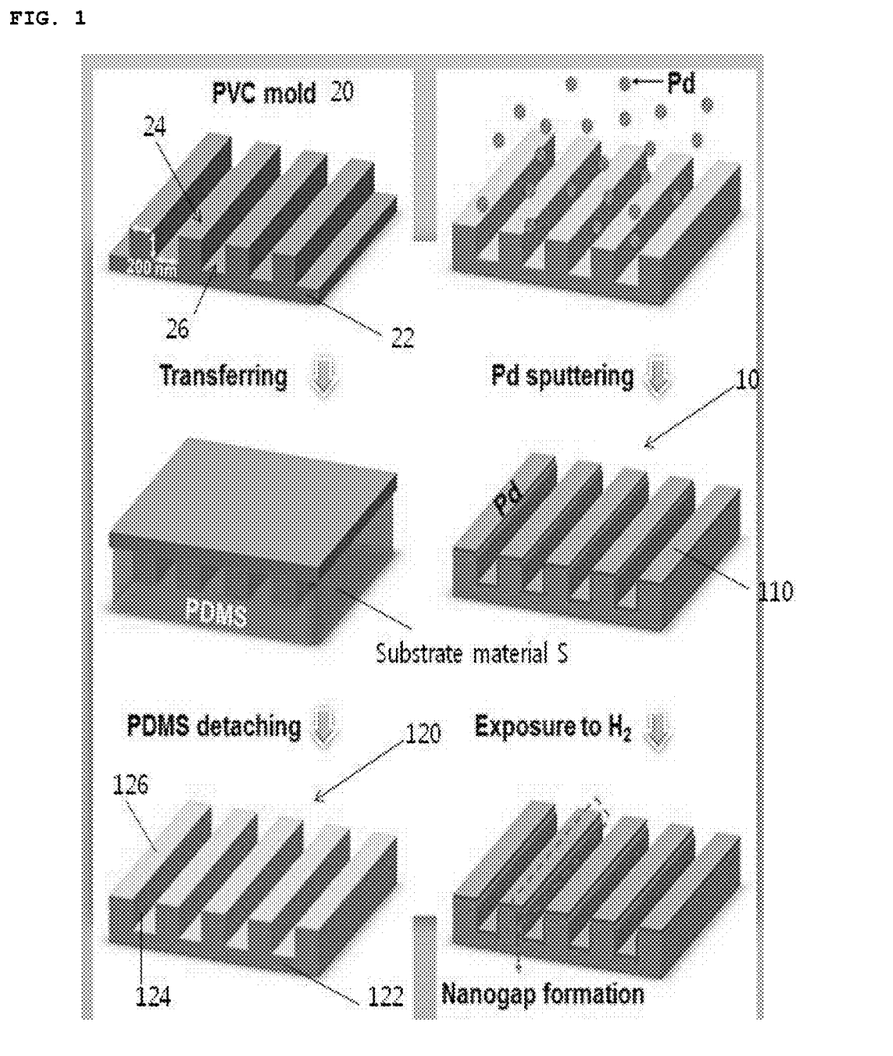
FIG. 1 is a schematic view showing a process of manufacturing a hydrogen sensor according to an embodiment of the present invention.

FIG. 1 schematically shows a process of manufacturing a hydrogen sensor according to an embodiment of the present invention.

As shown in FIG. 1, according to an embodiment of the present invention, a hydrogen sensor is manufactured using nanoimprinting technology. Specifically, a mold 20 having a pattern corresponding to nanogaps that are to be formed in a hydrogen sensor substrate is prepared. According to an embodiment of the present invention, the mold 20 that is employed is a PVC mold which has a base 22, a hydrogen detection part pattern 24 erected from the base 22, and a nanogap pattern 26 of naogaps formed between the hydrogen detection parts of the hydrogen detection part pattern 24. Here, according to an embodiment of the present invention, all of the height and width of the hydrogen detection part pattern 24 and the height and width of the nanogap pattern 26 are set to 200 nm (see FIG. 1). The hydrogen detection part pattern 24 can be formed integrally with the base 22, or be formed separately from and attached to the base 22. In other words, the method of forming the hydrogen detection part pattern according to the present invention is not specifically limited. It should also be understood that the material of the mold according to the present invention is not specifically limited. In addition, as is apparent to a person having ordinary skill in the art, the hydrogen sensor substrate 120 which is finally produced after the nanoimprinting, i.e. after the transfer processing that will be described later, has a base 122 corresponding to the base 22, a plurality of nanogaps 124 corresponding to the hydrogen detection part pattern 24, and a plurality of hydrogen detection parts 126 corresponding to the nanogap pattern 26.

Specifically, the patterns of the PVC mold are transferred to any material that is to form the hydrogen sensor substrate, for example, a transferable material S to which the patterns of the PVC mold can be transferred according to this embodiment by attaching the PVC mold to the transferable material S. The material S can be implemented as any material to which the patterns of the mold can be transferred, for example, an elastic material, such as natural rubber, synthetic resin, or polymer. Examples of the synthetic resin may include, but are not limited to, butadiene-based rubber, isoprene-based rubber, chloroprene-based rubber, nitrile-based rubber, polyurethane-based rubber and silicone-based rubber. Preferably, it is possible to use an elastic material, such as polydimethylsiloxane (PDMS, silicone rubber), which has good durability and low interfacial free energy. This facilitates shaping and machining of the transition metal or the alloy thereof that is disposed on the substrate. In addition to PDMS, it is possible to use a polyimide-based polymer, a polyurethane-based polymer, a fluorocarbon-based polymer, an acrylic-based polymer, a polyaniline-based polymer, a polyester-based polymer and the like. According to an embodiment of the present invention, PDMS was used. However, the present invention is not limited to the above-described flexible materials. Rather, inflexible materials, such as polyvinyl chloride (PVC), polyethylene terephthalate (PET) and polyethylene succinate (PES), can also be used, and the patterns of the mold can be transferred to these materials.

When the mold is detached from the transferable material after the transfer processing, the substrate material to which the patterns of the mold are transferred can be produced. The produced substrate material can then act as the hydrogen sensor substrate 120. Here, the hydrogen sensor substrate 120 has the nanogaps and the hydrogen detection parts that correspond to but are reverse to the patterns of the mold 20, as an obvious result of the transfer processing. Specifically, the hydrogen sensor substrate 120 has the base part 122 which corresponds to the base 22 of the mold 20, the plurality of hydrogen detection parts 126 which are erected from the base part 122 and correspond to the nanogap pattern 26 of the mold 20, and the plurality of nanogaps 124 which correspond to the hydrogen detection part pattern 24 of the mold and are formed between the hydrogen detection parts 126. Therefore, the height and width of the nanogaps 124 are 200 nm like the height and width of the hydrogen detection part pattern 24 of the mold 20.

Figure 2:
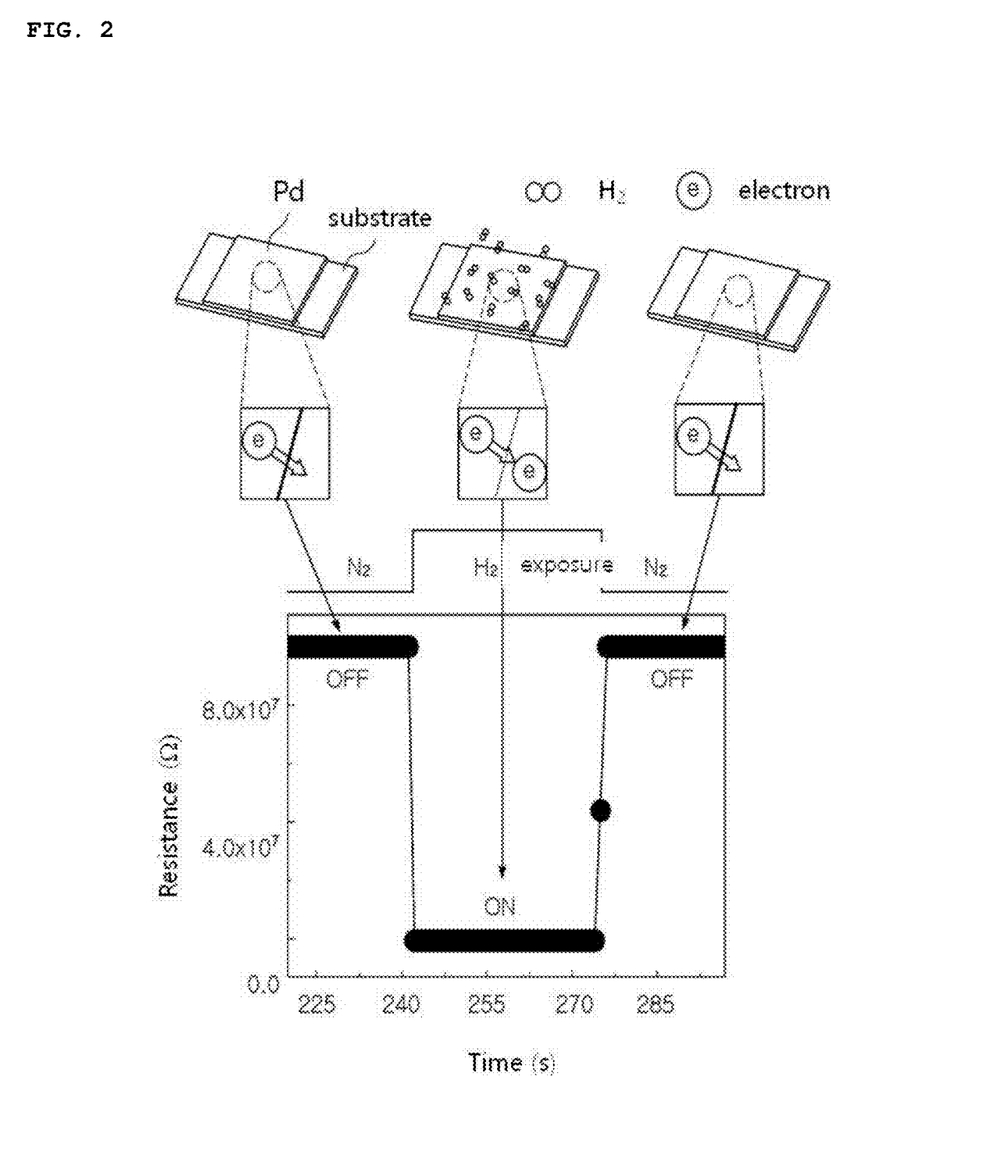
FIG. 2 is an explanatory view depicting variations in resistance of the hydrogen sensor according to an embodiment of the present invention depending on whether or not hydrogen is present.
Figure 4:
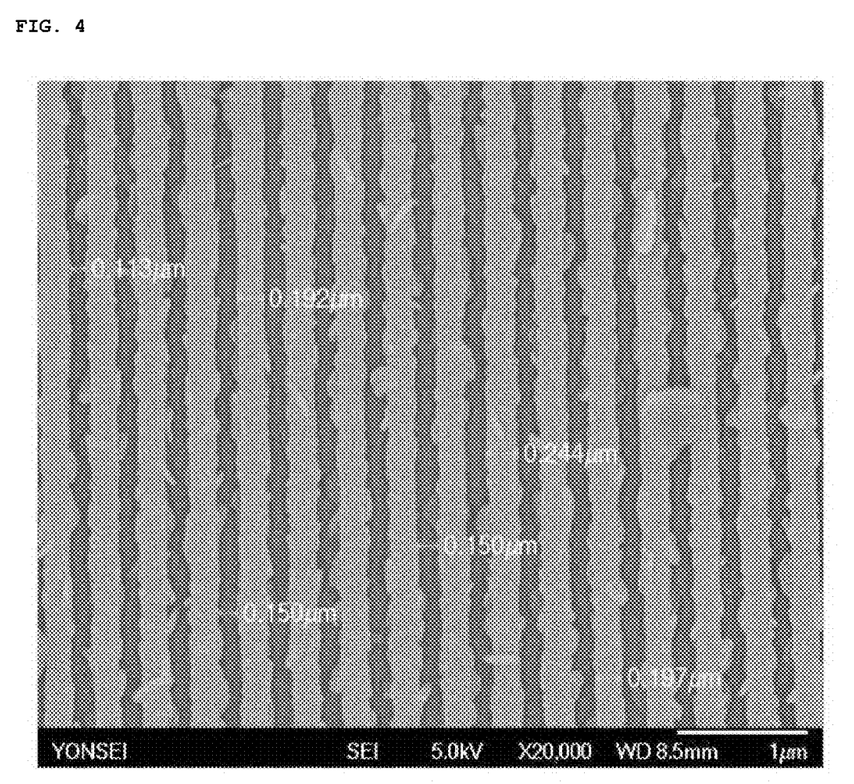
FIG. 4 is a microscopy picture showing a hydrogen sensor substrate prepared according to an embodiment of the present invention.

A hydrogen sensor 10 (electrodes are not shown) is completed by forming a thin film 110 made of a transition metal or an alloy thereof on the hydrogen sensor substrate 120 which is prepared according to the above-described process. According to an embodiment of the present invention, a Pd thin film is formed. A microscopy picture of the PD thin film on which the nanogaps are formed according to the above-described process is shown in FIG. 4. Here, according to the present invention, materials for the thin film are not specifically limited. Any thin film can be used as long as it is made of a transition metal that can be expanded by hydrogen or an alloy thereof. Specifically, as shown in FIG. 2, when the nanogaps are formed in the thin film made of a transition metal or an alloy thereof according to the above-described method, the nanogaps prevent a smooth flow of current, thereby creating a high resistance. However, in a hydrogen atmosphere, hydrogen is absorbed, thereby increasing the volume. Due to the increased volume, the nanogaps are filled up, thereby decreasing the resistance. The concentration of hydrogen can be measured by measuring a variation in the resistance depending on presence/absence of hydrogen gas. Therefore, according to the present invention, the thin film made of a transition metal that can be expanded by hydrogen and an alloy thereof can be used.

For instance, the transition metal may be one transition metal selected from among, but not limited to, Pd, Pt, Ni, Ag, Ti, Fe, Zn, Co, Mn, Au, W, In and Al that can be expanded by hydrogen.

In addition, the alloy can be selected from among, but not limited to, Pd—Ni, Pt—Pd, Pd—Ag, Pd—Ti, Pd—Fe, Pd—Zn, Pd—Co, Pd—Mn, Pd—Au, Pd—W, Pt—Ni, Pt—Ag, Pt—Ag, Pt—Ti, Fe—Pt, Pt—Zn, Pt—Co, Pt—Mn, Pt—Au and Pt—W that can be expanded by hydrogen. For instance, in the case of a Pd—Ni or Pd—Au alloy, Pd acts as a catalyst in a reaction with hydrogen, and Ni or Au reduces the lattice constant of Pd. This consequently increases the durability of the hydrogen sensor made of the Pd—Ni or Pd—Au alloy and reduces the time required to react with hydrogen. More preferably, the transition metal and the alloy thereof are respectively implemented as Pd and an alloy thereof.

In the meantime, the process of forming the thin film 110 made of the transition metal or the alloy thereof on the hydrogen sensor substrate 120 can be implemented using any of methods that are typically used in the art. For instance, it is possible to use physical deposition, such as sputtering or evaporation, chemical vapor deposition, atomic layer deposition (ALD), or the like. According to this embodiment, the Pd thin film is deposited via sputtering.

Figure 3:
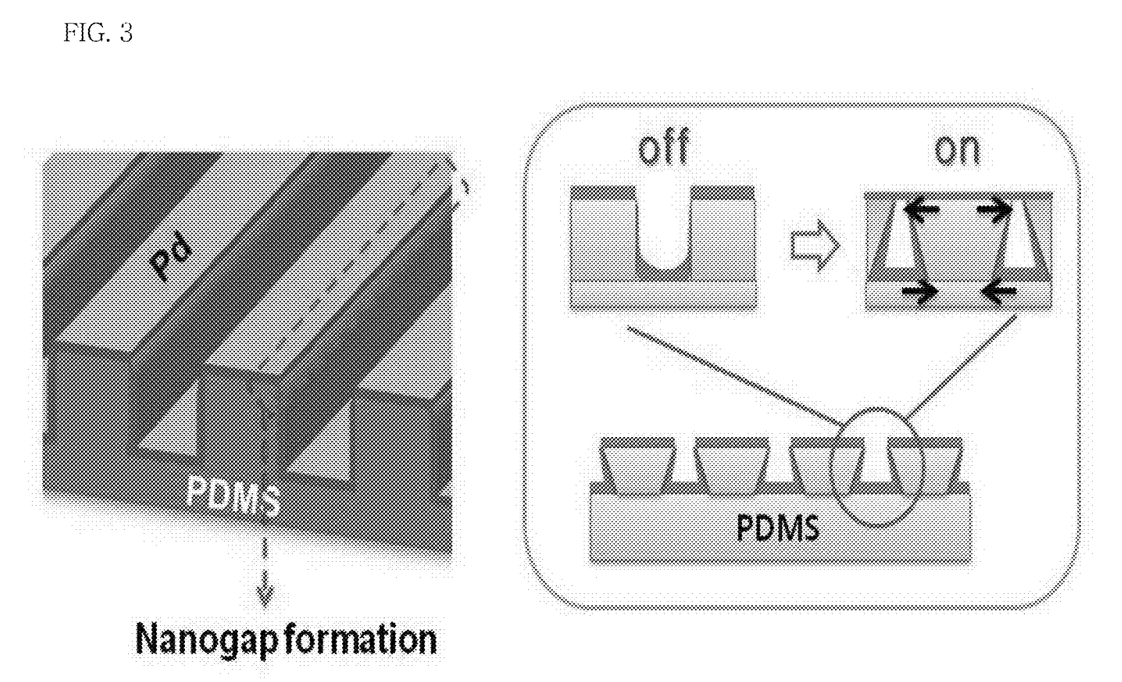
FIG. 3 is a schematic view showing a phenomenon that occurs in nanogaps during the absorption of hydrogen to the hydrogen sensor according to an embodiment of the present invention.

Describing this phenomenon in more detail with reference to FIG. 3, the hydrogen detection parts 126 are spaced apart from each other with the nanogaps 124 being interposed therebetween. However, in the hydrogen atmosphere, when hydrogen is absorbed to the Pd thin film 110, the Pd thin film expands. Consequently, hydrogen detection parts 126 are connected to each other on both sides of the nanogaps 124, so that that current flows between the hydrogen detection parts 126, thereby detecting hydrogen (on). (At this time, each upper portion of the hydrogen detection parts expands and each lower portion of the hydrogen detection parts contracts, as shown in FIG. 3.) Afterwards, when the hydrogen atmosphere is removed, the Pd thin film 110 contracts, such that the connected hydrogen detection parts 126 are spaced apart from each other on both sides of the nanogaps 124, so that no current flows between the hydrogen detection parts 126 (off). Accordingly, the hydrogen sensor 10 which is manufactured as above according to an embodiment of the present invention acts as an on-off sensor.

Figure 5:
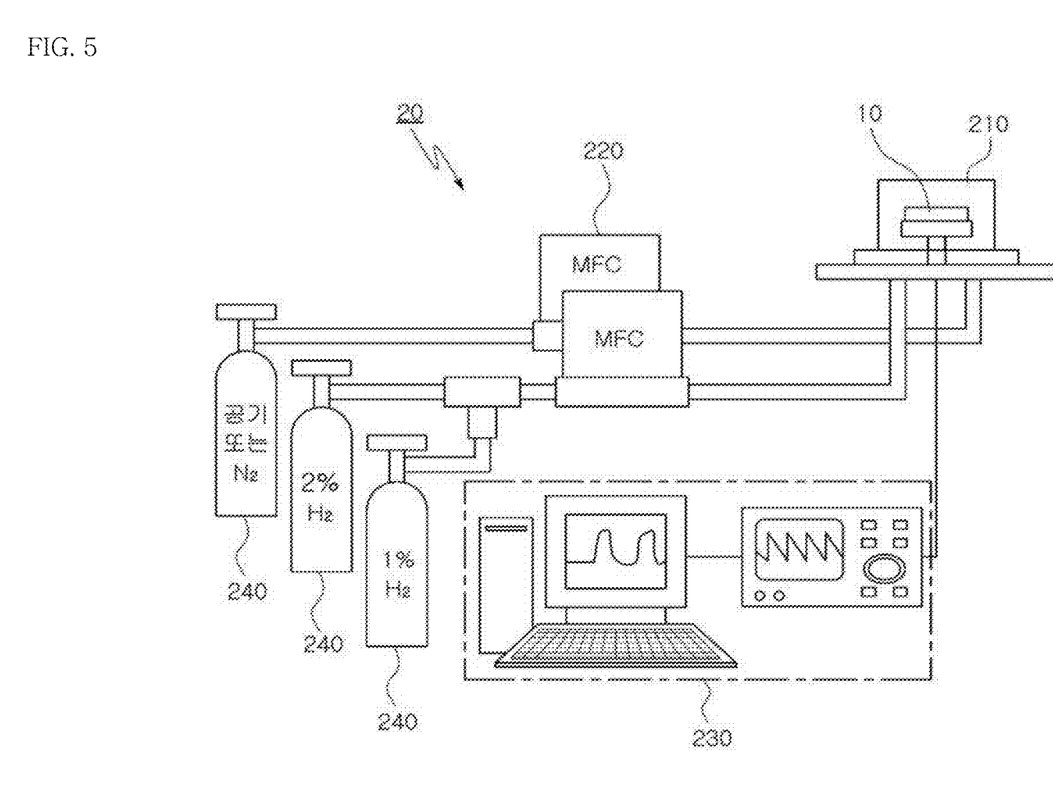
FIG. 5 is a schematic view showing a system for measuring hydrogen detection performance of the hydrogen sensor according to an embodiment of the present invention.

In order to evaluate the characteristics of the hydrogen sensor which is manufactured according to the above-described process, the system shown in FIG. 5 is used. This system can obtain measurements using a quasi-two probe method.

The system is the I-V measurement system shown in FIG. 5, and includes a reaction chamber 210, a mass flow controller 220 which adjusts the flow rate of $H_2$ and $N_2$ gases, a device 230 for inducing a voltage and current to the sensor, and a gas tank 240. The hydrogen sensor 10 which is manufactured according to the above-described embodiment of the present invention is disposed inside the reaction chamber 210.

In this system 20, the reaction chamber 210, inside of which the hydrogen sensor 10 is disposed, serves to seal the hydrogen sensor 10 from the outside when the sensor reacts with the $H_2$ gas. The MFC 220 accurately adjusts the flow rate of the $H_2$ and $N_2$ gases, so that setting the concentration of the $H_2$ gas can have a desired ratio. The $H_2$ gas, the concentration of which is adjusted, reacts with the hydrogen sensor 10 inside the reaction chamber 210. At this time, an electrical signal in response to changes in the sensor is measured by the device 230, which induces a voltage and current to the sensor.

Measurement was carried out at room temperature and ambient pressure. After the Pd thin film hydrogen sensor 10 having the nanogaps was loaded inside the reaction chamber 210, which was connected to an external current-inducing device, a mixture, in which the $H_2$ and $N_2$ gases were mixed, was flown into the chamber. Then, the intensity of current was measured while inducing a voltage of 0.1V.

Figure 6:
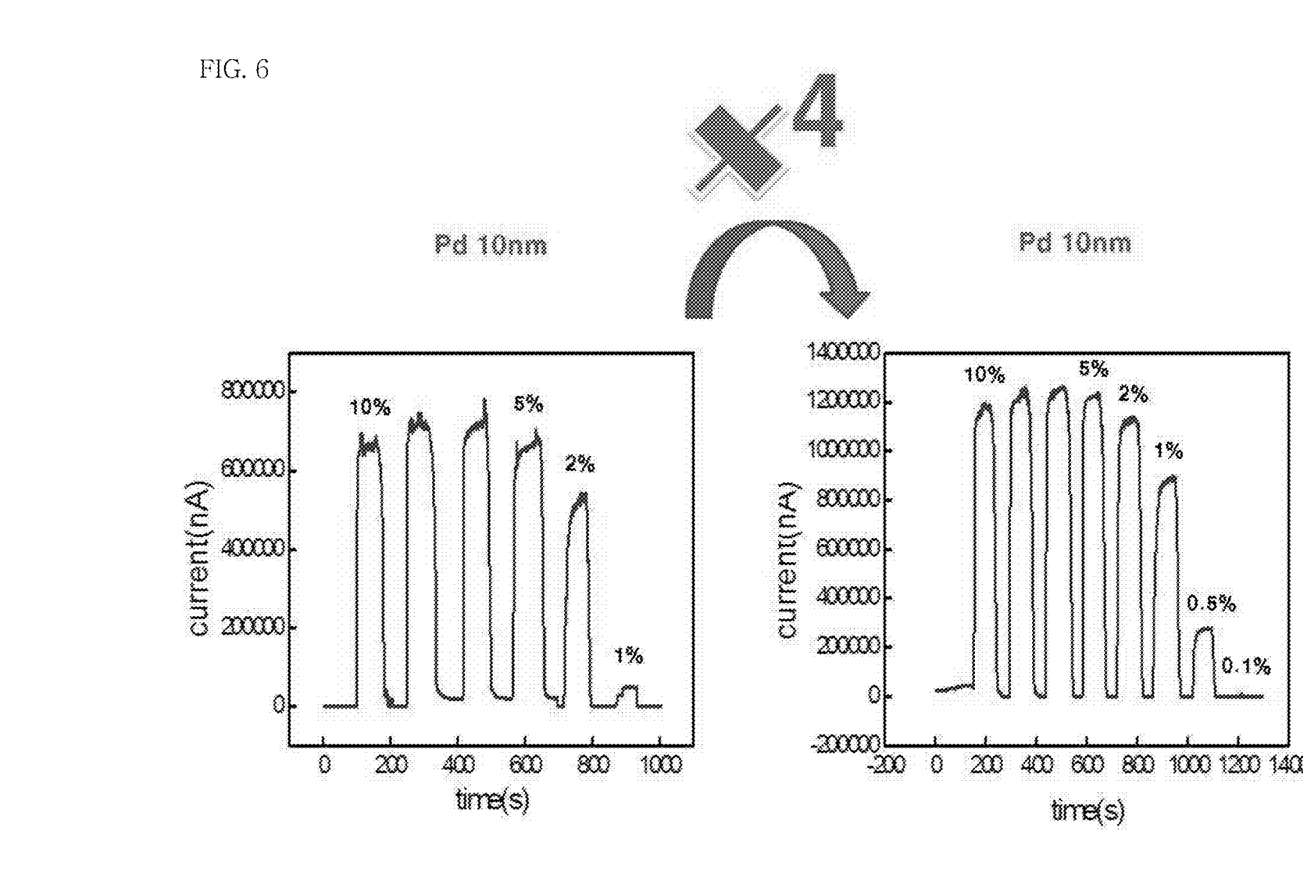
FIG. 6 is a view showing that a hydrogen sensor which is manufactured by increasing the area four times is also properly functioning.

FIG. 6 shows the characteristics of a hydrogen sensor depending on the size, in which the thickness of the Pd thin film is 10 nm. Referring to FIG. 6, the hydrogen sensor properly acts as an on-off sensor when the size is increased four times. This exhibits that a hydrogen sensor having a large area can also be properly manufactured when it is manufactured according to the method of the present invention.

As described above, the material of the hydrogen sensor substrate 120 according to the present invention is not specifically limited. The material is not limited to the elastic material, i.e. the flexible material, of the foregoing embodiment, and can be implemented as any material to which the patterns of the mold can be transferred. Thus, the inventors have manufactured a hydrogen sensor according to the above-described process by employing an inflexible material, such as PVC, as the material of the hydrogen sensor substrate. In this case, as shown in FIG. 7, the thicknesses of the Pd thin films were 4 nm, 5 nm and 10 nm.

Figure 7:
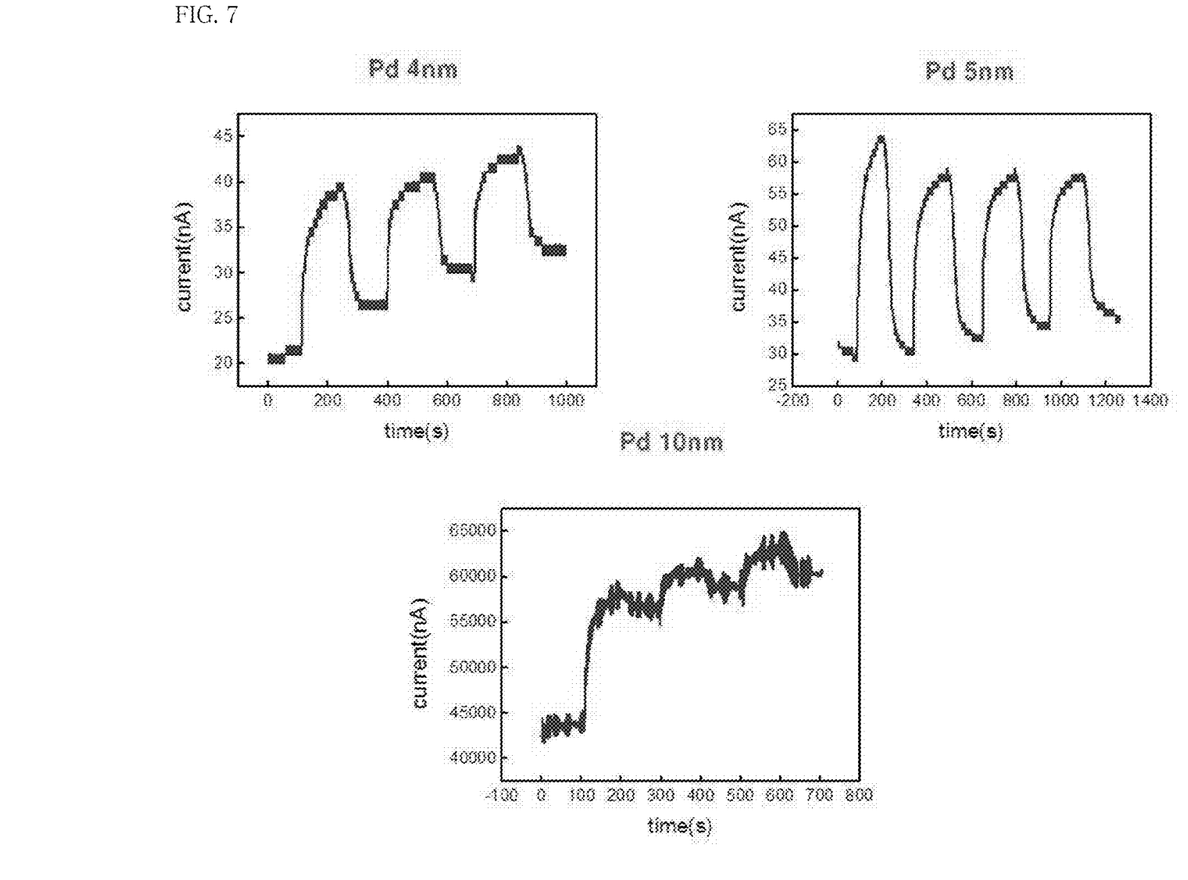
FIG. 7 is a view showing the hydrogen detection performance of a hydrogen sensor having a hydrogen sensor substrate which is made of an inflexible material, in which the hydrogen sensor can be used as an on-current sensor.

As can be appreciated from FIG. 7, when the hydrogen sensor substrate is made of an inflexible material (PVC), reaction characteristics are different from the foregoing embodiment in which the hydrogen sensor substrate 120 is made of a flexible material. Specifically, in the foregoing embodiment, the hydrogen detection parts 126 are attached to each other due to the absorption of hydrogen (on), and when the hydrogen atmosphere is removed, the hydrogen detection parts 126 return to the original position so that the nanogaps 124 return to the original position (off). In contrast, in the case where the hydrogen sensor substrate is made of PVC, the thin film properly expands due to the absorption of hydrogen, but when the hydrogen atmosphere is removed, the nanogaps 124 do not return to the original position. It seems that, although the thin film expands and contracts, a behavior different from that of the foregoing embodiment is caused by the inflexible material of the hydrogen detection parts, and the off state is not correctly realized. Therefore, when the hydrogen sensor substrate is made of an inflexible material, it is preferable to use the hydrogen sensor as an on-current sensor which only detects hydrogen. That is, the hydrogen sensor can be constructed by selecting a flexible material or an inflexible material for the hydrogen sensor substrate depending on the use.

Figure 8:
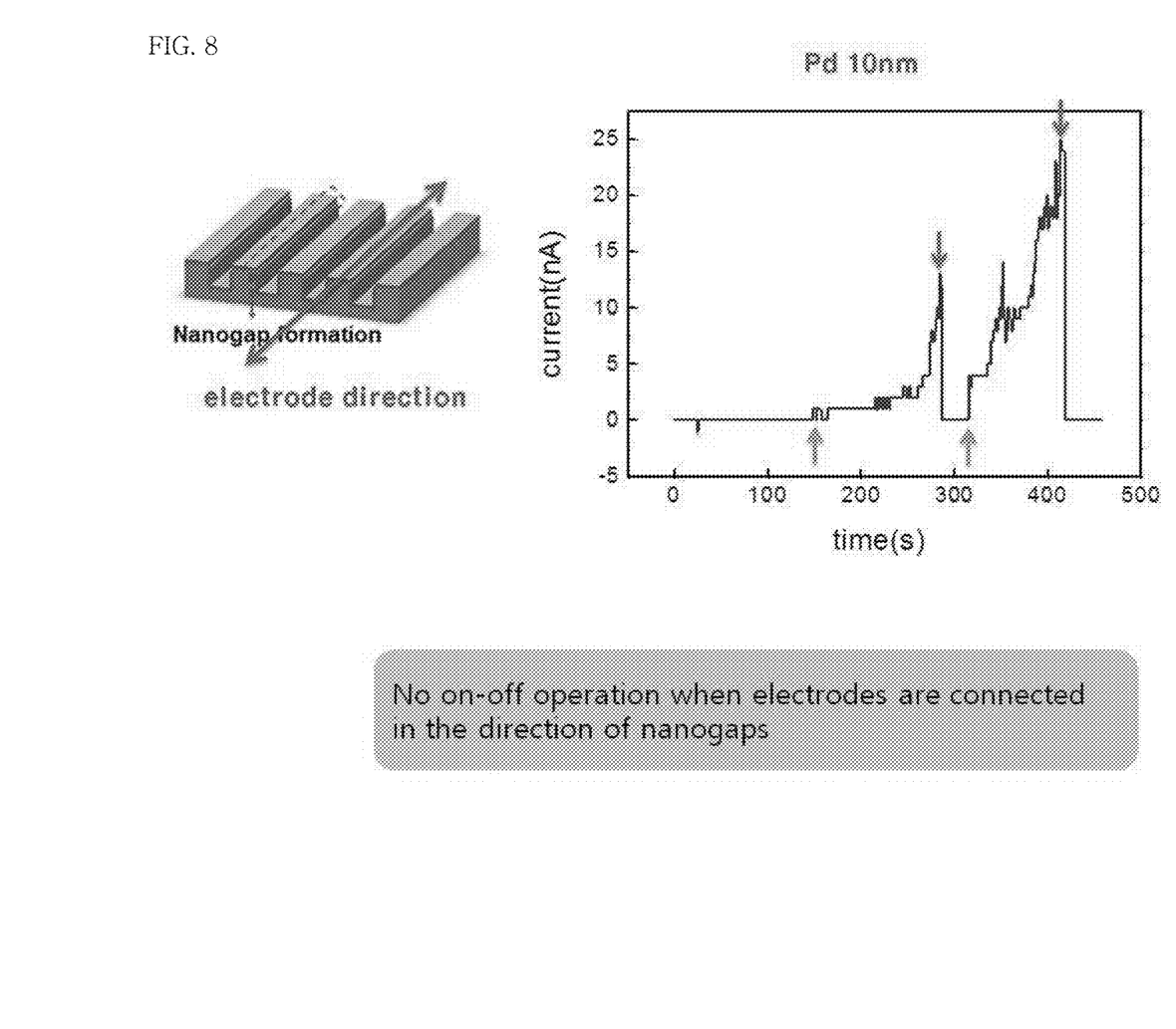
FIG. 8 is a view showing the hydrogen detection performance of a hydrogen sensor having electrodes connected in the longitudinal direction of nanogaps, in which the hydrogen sensor does not properly operate as an on-off sensor.
Figure 9:
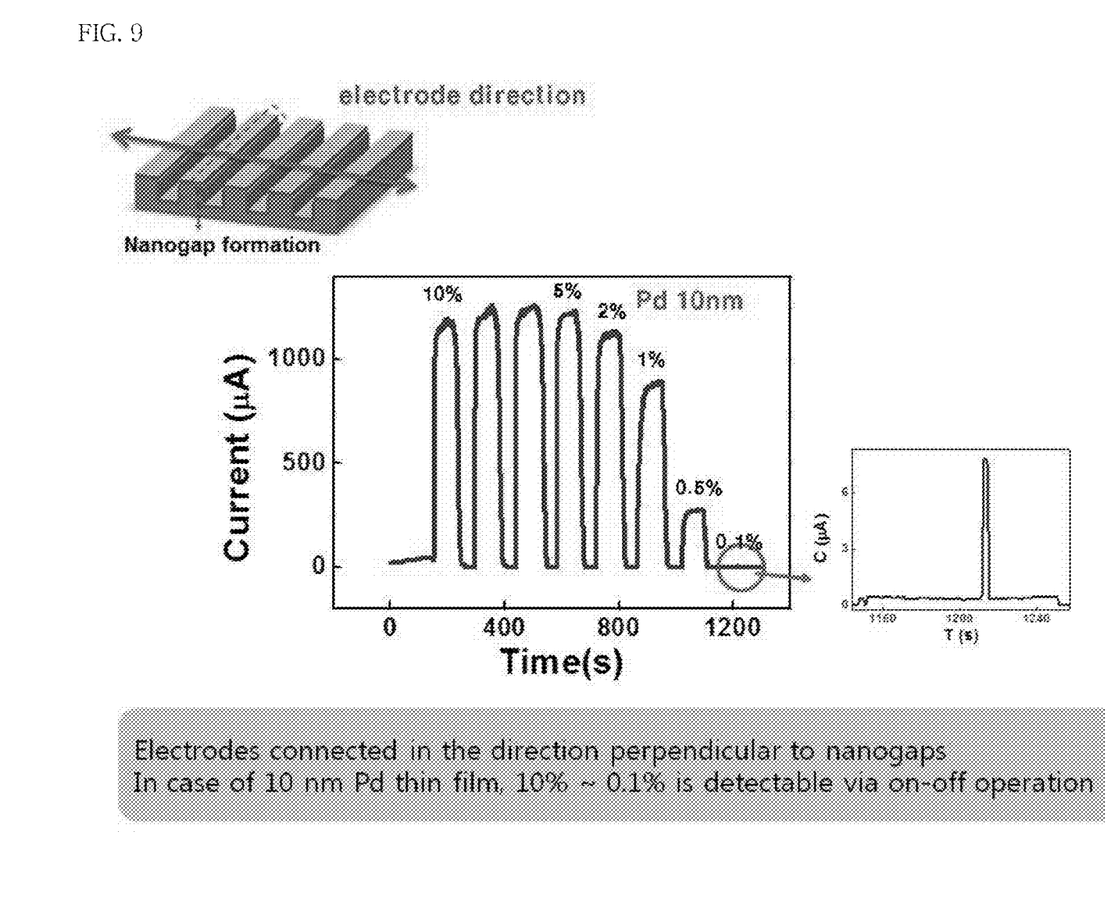
FIG. 9 is a view showing the hydrogen detection performance of a hydrogen sensor having electrodes connected in the direction perpendicular to the longitudinal direction of nanogaps, in which the hydrogen sensor properly operates as an on-off sensor.

In addition, the inventors observed characteristics depending on the direction in which the nanogaps are connected to the electrodes, and the results are presented in FIG. 8 and FIG. 9. FIG. 8 shows the characteristics of a hydrogen sensor when the electrodes are connected in the longitudinal direction of the nanogaps. As shown in FIG. 8, the hydrogen sensor does not properly operate as an on-off sensor. In contrast, as shown in FIG. 9, when the electrodes are connected in the direction perpendicular to the longitudinal direction of the nanogaps, the hydrogen sensor can detect a hydrogen concentration ranging from 10% to 0.1%. Therefore, according to an exemplary embodiment of the present invention, the electrodes are connected in the direction perpendicular to the longitudinal direction of the nanogaps.

Figure 10:
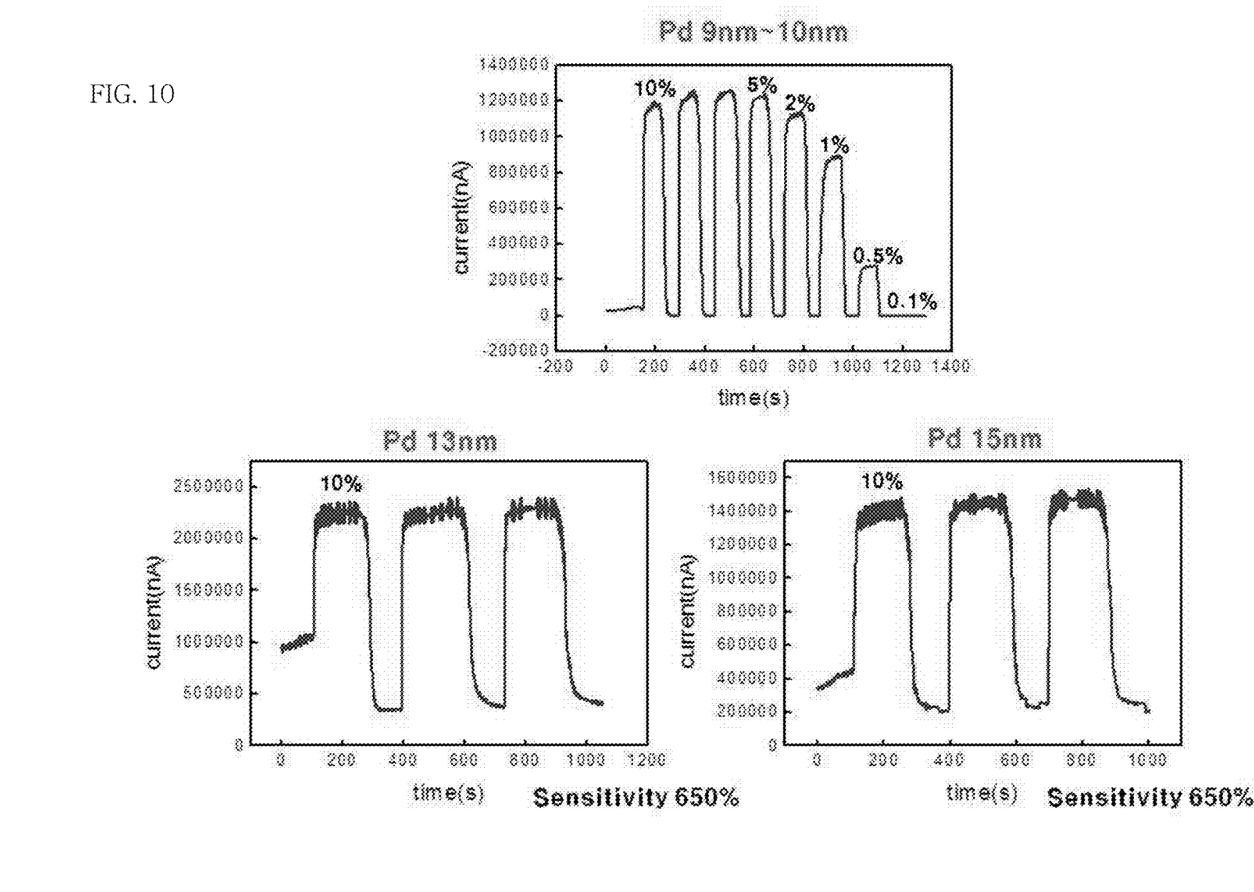
FIG. 10 is a view showing the hydrogen detection performance of a hydrogen sensor measured by varying the thickness of a Pd thin film, in which the hydrogen sensor does not properly operate as an on-off sensor when the thickness of the film exceeds about 12 nm.

Furthermore, the inventors investigated the influence of the thickness of the thin film on the detection performance of the hydrogen sensor, and the results are shown in FIG. 10. As shown in FIG. 10, it can be appreciated that, when the thickness of the thin film exceeds about 12 nm, the current does not decrease to 0. That is, the thin film expands due to the absorption of hydrogen, so that the hydrogen detection parts are attached to each other, thereby filling up the nanogaps, whereas the attached hydrogen detection parts are not easily detached from each other. Thus, the hydrogen sensor does not act as an on-off sensor but acts only as an on sensor. Consequently, it is required to set the thickness of the thin film to 12 nm or less in order to realize a hydrogen sensor which acts as an on-off sensor. Although not specifically shown in the figures, when the thickness of the thin film is 8 nm or less, it was observed that the hydrogen detection parts were not properly attached to each other since the expansion of the thin film was reduced despite of the absorption of hydrogen. Therefore, it is preferred that the thickness of the thin film be 8 nm or more. As shown in the figure, when the thickness of the thin film ranges from 9 nm to 10 nm, the hydrogen sensor can optimally operate, and thus detect a hydrogen concentration of 0.1%. Accordingly, the thin film be formed at a thickness ranging, preferably, from 8 nm to 12 nm, and more preferably, from 9 nm to 10 nm.

Figure 11:
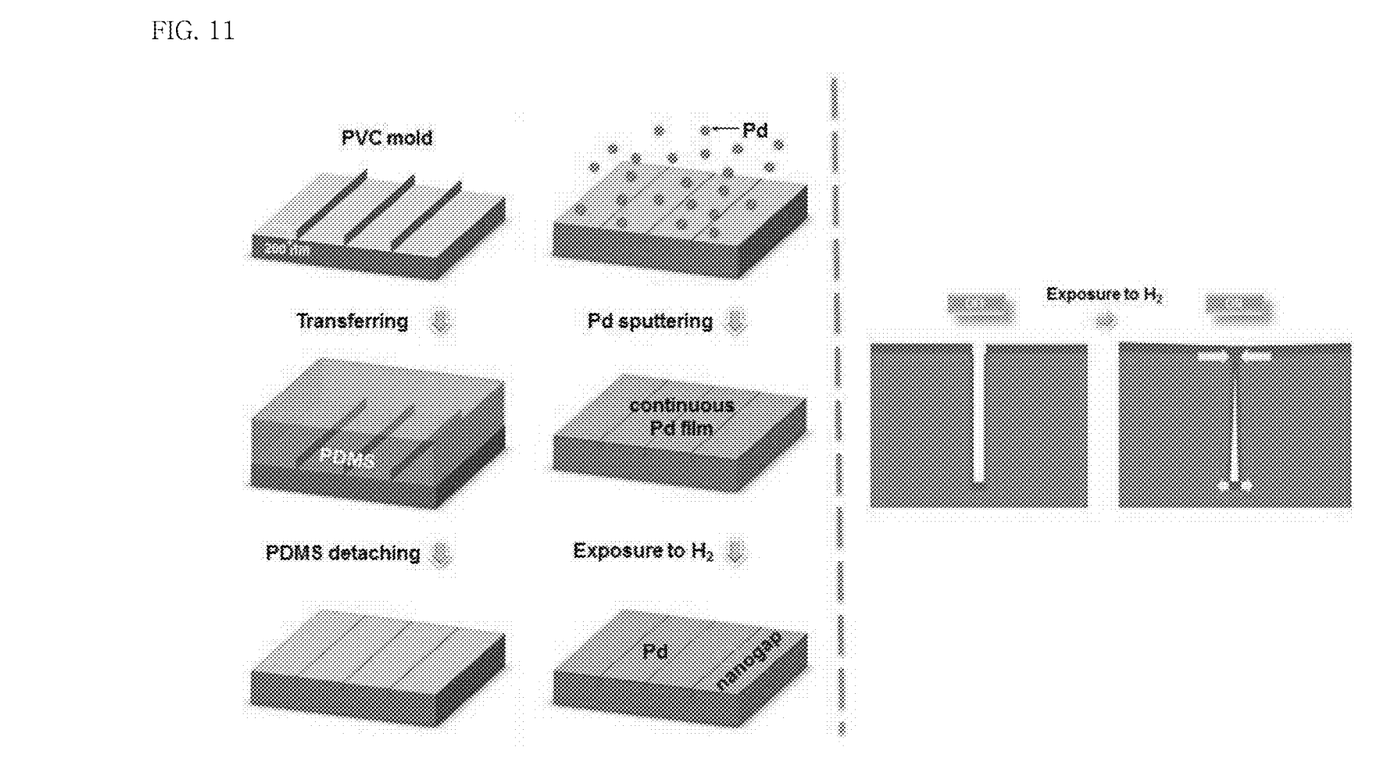
FIG. 11 is a schematic view showing the process of manufacturing a hydrogen sensor according to another embodiment of the present invention.

According to the embodiment shown in FIG. 1, the ratio of the height to the width of the nanogap is substantially 1:1. However, as shown in FIG. 11, when the width of the nanogaps is smaller than the height of the nanogaps, i.e. the ratio of the height to the width of the nanogaps is 1:x, where x<1, preferably, x<<1, the nanodetection parts can be more easily attached to each other. This configuration is preferable, since lower concentrations of hydrogen can also be detected.

The foregoing descriptions of specific exemplary embodiments of the present invention have been presented for the purposes of illustration and description. They are not intended to be exhaustive or to limit the present invention to the precise forms disclosed, and obviously many modifications and variations are possible in light of the above teachings. The exemplary embodiments were chosen and described in order to explain certain principles of the present invention and their practical application, to thereby enable others skilled in the art to make and utilize various exemplary embodiments of the present invention, as well as various alternatives and modifications thereof. It is intended that the scope of the present invention be defined by the Claims appended hereto and their equivalents.

The invention claimed is:

1. A method of manufacturing a hydrogen sensor, the method comprising the steps of:
    preparing a mold which has a hydrogen detection part pattern, a nanogap pattern and a base which are to be formed on a hydrogen sensor substrate;
    preparing a material to which the patterns of the mold are transferrable;
    forming the hydrogen sensor substrate by bringing the mold into contact with the material to thus transfer the patterns of the mold to the material and then detaching the mold from the material to which the patterns are transferred, the hydrogen sensor substrate having a base part which corresponds to the base of the mold, a plurality of hydrogen detection parts which is erected from the base part and corresponds to the nanogap pattern, and a plurality of nanogaps which is formed between the hydrogen detection parts and corresponds to the hydrogen detection part pattern; and
    forming a thin film on the hydrogen sensor substrate, the thin film being made of a transition metal or an alloy thereof which is to be expanded by hydrogen,
    wherein no tensile stress is applied during the manufacturing of the hydrogen sensor.

2. The method according to claim 1, wherein the hydrogen sensor substrate is made of a flexible material or an inflexible material.

3. The method according to claim 2, wherein the hydrogen sensor substrate is made of the inflexible material of polyvinyl chloride (PVC), polyethylene terephthalate (PET) or polyethylene succinate (PES).

4. The method according to claim 3, wherein the hydrogen sensor is used as an on-current sensor.

5. The method according to claim 2, wherein the hydrogen sensor substrate is made of natural rubber, synthetic resin or polymer.

6. The method according to claim 5, wherein the synthetic resin is one selected from among butadiene-based rubber, isoprene-based rubber, chloroprene-based rubber, nitrile-based rubber, polyurethane-based rubber and silicone-based rubber.

7. The method according to claim 6, wherein the synthetic resin is polydimethylsiloxane (PDMS).

8. The method according to claim 1, wherein the transition metal is one transition metal selected from among Pd, Pt, Ni, Ag, Ti, Fe, Zn, Co, Mn, Au, W, In and Al.

9. The method according to claim 1, wherein the alloy is one selected from among Pd—Ni, Pt—Pd, Pd—Ag, Pd—Ti, Pd—Fe, Pd—Zn, Pd—Co, Pd—Mn, Pd—Au, Pd—W, Pt—Ni, Pt—Ag, Pt—Ag, Pt—Ti, Fe—Pt, Pt—Zn, Pt—Co, Pt—Mn, Pt—Au and Pt—W that can be expanded by hydrogen.

10. The method according to claim 8, wherein a thickness of the transition metal ranges from 8 nm to 12 nm.

11. The method according to claim 1, further comprising the step of connecting electrodes in a direction perpendicular to a longitudinal direction of the nanogaps.

12. The method according to claim 1, wherein a ratio of a height to a width of the nanogaps is 1:x, where x<1.

* * * * *